United States Patent
Shaya (12)

(10) Patent No.: US 10,694,144 B2
(45) Date of Patent: Jun. 23, 2020

(54) SYSTEM, METHOD AND APPARATUS FOR PERFORMING REAL-TIME VIRTUAL MEDICAL EXAMINATIONS

(71) Applicant: Fawzi Shaya, West Bloomfield, MI (US)

(72) Inventor: Fawzi Shaya, West Bloomfield, MI (US)

( * ) Notice: Subject to any disclaimer, the term of this patent is extended or adjusted under 35 U.S.C. 154(b) by 0 days.

(21) Appl. No.: 15/655,998

(22) Filed: Jul. 21, 2017

(65) Prior Publication Data
US 2017/0324930 A1 Nov. 9, 2017

Related U.S. Application Data

(63) Continuation of application No. 13/165,052, filed on Jun. 21, 2011, now abandoned.
(Continued)

(51) Int. Cl.
*A61B 5/00* (2006.01)
*G06F 19/00* (2018.01)
(Continued)

(52) U.S. Cl.
CPC ........ *H04N 7/141* (2013.01); *A61B 5/0022* (2013.01); *A61B 5/7465* (2013.01); *G06F 19/3418* (2013.01); *G06Q 10/10* (2013.01); *G06Q 30/0241* (2013.01); *G06Q 50/22* (2013.01); *G16H 10/60* (2018.01); *A61B 5/021* (2013.01); *A61B 5/0402* (2013.01); *A61B 5/087* (2013.01); *A61B 5/14532* (2013.01); *A61B 5/14542* (2013.01); *G16H 15/00* (2018.01)

(58) Field of Classification Search
CPC .... H04N 7/141; G06Q 50/22; G06Q 30/0241; G16H 15/00; G16H 10/60; G06C 30/0241; A61B 5/021; A61B 5/0022; A61B 5/087; A61B 5/0402; A61B 5/7465; A61B 5/14532; A61B 5/14542
See application file for complete search history.

(56) References Cited

U.S. PATENT DOCUMENTS 5,961,446 A  10/1999 Beller et al.
5,987,519 A  11/1999 Peifer et al.
(Continued)

FOREIGN PATENT DOCUMENTS

WO   01/47418 A1   7/2001

OTHER PUBLICATIONS

Bluegiga Technologies "Bluetooth® Health Device Profile" Aug. 2009, https://www.semiconductorstore.com/pdf/NewSite/Bluegiga/Bluegiga_Bluetooth_Health_Device_Profile.pdf (Year: 2009).*

*Primary Examiner* — Boniface N Nganga
(74) *Attorney, Agent, or Firm* — Honigman LLP

(57) ABSTRACT

Disclosed herein is a method for permitting a real-time virtual medical examination using a patient device and at least one diagnostic device including receiving, at the patient device, a signal transmitted from the at least one diagnostic device; generating diagnostic information based on the received signal; encrypting the diagnostic information; establishing communication over a network between the patient device and a first remote server; establishing a video conferencing session via a second remote server; and transmitting the encrypted diagnostic information to the first remote server.

15 Claims, 6 Drawing Sheets

Related U.S. Application Data

(60) Provisional application No. 61/369,461, filed on Jul. 30, 2010.

(51) Int. Cl.

| | | |
|---|---|---|
| *G06Q 50/22* | (2018.01) | |
| *A61B 5/021* | (2006.01) | |
| *A61B 5/0402* | (2006.01) | |
| *A61B 5/087* | (2006.01) | |
| *A61B 5/145* | (2006.01) | |
| *H04N 7/14* | (2006.01) | |
| *G06Q 10/10* | (2012.01) | |
| *G06Q 30/02* | (2012.01) | |
| *G16H 10/60* | (2018.01) | |
| *G16H 15/00* | (2018.01) | |

(56) References Cited

U.S. PATENT DOCUMENTS

| | | | |
|---|---|---|---|
| 5,997,476 A | 12/1999 | Brown | |
| 6,038,469 A | 3/2000 | Karlsson et al. | |
| 6,064,968 A | 5/2000 | Schanz | |
| 6,112,224 A | 8/2000 | Peifer et al. | |
| 6,366,871 B1 | 4/2002 | Geva | |
| 6,369,847 B1 | 4/2002 | James et al. | |
| 6,409,660 B1 | 6/2002 | Sjoqvist | |
| 6,610,010 B2 | 8/2003 | Sjoqvist | |
| 6,640,239 B1 * | 10/2003 | Gidwani | H04L 29/06027 370/353 |
| 6,820,057 B1 | 11/2004 | Loch et al. | |
| 7,158,861 B2 | 1/2007 | Wang et al. | |
| 7,222,054 B2 | 5/2007 | Geva | |
| 7,232,220 B2 | 6/2007 | Franz et al. | |
| 7,257,158 B1 | 8/2007 | Figueredo et al. | |
| 7,283,153 B2 | 10/2007 | Provost et al. | |
| 7,412,396 B1 | 8/2008 | Haq | |
| 7,425,977 B2 | 9/2008 | Sakai | |
| 7,520,611 B2 | 4/2009 | Franz et al. | |
| 7,618,368 B2 | 11/2009 | Brown | |
| 7,624,028 B1 | 11/2009 | Brown | |
| 7,650,291 B2 | 1/2010 | Rosenfeld et al. | |
| 7,657,444 B2 | 2/2010 | Yu | |
| 7,761,261 B2 | 7/2010 | Shmueli et al. | |
| 7,761,312 B2 | 7/2010 | Brown | |
| 9,210,200 B1 * | 12/2015 | Chapweske | H04L 65/4038 |
| 2002/0065682 A1 | 5/2002 | Goldenberg | |
| 2002/0118809 A1 * | 8/2002 | Eisenberg | H04L 12/1813 379/202.01 |
| 2003/0028399 A1 | 2/2003 | Davis et al. | |
| 2003/0069752 A1 | 4/2003 | LeDain et al. | |
| 2005/0246185 A1 * | 11/2005 | Brown | G06Q 10/00 705/2 |
| 2006/0036134 A1 | 2/2006 | Tarassenko et al. | |
| 2006/0074709 A1 | 4/2006 | McAllister | |
| 2006/0122466 A1 | 6/2006 | Nguyen-Dobinsky et al. | |
| 2006/0173267 A1 | 8/2006 | Chiang et al. | |
| 2006/0271400 A1 | 11/2006 | Clements et al. | |
| 2007/0073520 A1 | 3/2007 | Bleines | |
| 2007/0130287 A1 | 6/2007 | Kumar et al. | |
| 2007/0192910 A1 * | 8/2007 | Vu | B25J 5/007 700/245 |
| 2008/0095079 A1 * | 4/2008 | Barkley | H04L 12/1827 370/260 |
| 2008/0113621 A1 | 5/2008 | Parthasarathy | |
| 2008/0275311 A1 | 11/2008 | Haq | |
| 2009/0012373 A1 | 1/2009 | Raij et al. | |
| 2009/0093688 A1 | 4/2009 | Mathur | |
| 2009/0112070 A1 | 4/2009 | Lin et al. | |
| 2009/0146822 A1 | 6/2009 | Soliman | |
| 2009/0149767 A1 | 6/2009 | Rossetti | |
| 2009/0167842 A1 | 7/2009 | Sandhu | |
| 2009/0240525 A1 | 9/2009 | Sadler et al. | |
| 2009/0264712 A1 | 10/2009 | Baldus et al. | |
| 2010/0030580 A1 | 2/2010 | Salwan | |
| 2010/0128104 A1 | 5/2010 | Fabregat et al. | |
| 2010/0137693 A1 | 6/2010 | Porras et al. | |
| 2010/0205541 A1 * | 8/2010 | Rapaport | G06Q 10/10 715/753 |
| 2010/0325209 A1 * | 12/2010 | Thapa | H04L 45/00 709/204 |
| 2011/0015494 A1 | 1/2011 | Spaulding | |
| 2011/0106557 A1 * | 5/2011 | Gazula | G06Q 10/10 705/3 |

\* cited by examiner

SYSTEM, METHOD AND APPARATUS FOR PERFORMING REAL-TIME VIRTUAL MEDICAL EXAMINATIONS

CROSS-REFERENCE TO RELATED APPLICATIONS

This application is a continuation application of U.S. application Ser. No. 13/165,052, filed on Jun. 21, 2011, which is a non-provisional application claiming priority to U.S. Provisional Patent Application No. 61/369,461, filed Jul. 30, 2010, the entire contents of each of which are hereby incorporated by reference.

TECHNICAL FIELD

The disclosure generally relates to remote medical diagnostic and monitoring systems and solutions in which a physician conducts an examination of a remotely located patient, and more specifically, to a system and method for performing virtual medical examinations using secure videoconferencing and the secure transmission and receipt of patient diagnostic information.

BACKGROUND

Access to medical care providers remains a challenge for many patient populations, both due to cost and lack of geographic proximity. Patient populations in rural areas, especially those in third world countries, will likely find themselves without adequate numbers of local treating physicians for decades to come. Many patients are house-bound and cannot easily travel to a medical clinic. In addition, certain types of specialists (e.g., neurologists) are often in short supply, leaving some patient populations underserved.

Telemedicine systems have been proposed as a way of remotely diagnosing and treating patients using telephonic communications. However, known systems typically suffer from several drawbacks. First, many of them lack adequate safeguards to protect the confidentiality of patient medical information. In the United States, the Health Insurance Portability and Accountability Act of 1996 ("HIPAA") requires entities exchanging health care information to enact appropriate safeguards to protect the confidentiality of electronically transmitted patient information. Many prior telemedicine systems do not allow patients and physicians to communicate in real time in a manner that protects their communications from third parties.

In addition, many known telemedicine systems lack a mechanism for conveniently and securely transmitting patient diagnostic information, such as blood pressure data, pulse oxymeter data, spirometer data, stethoscope data, pulse and blood gas analysis, weight, electrocardiograph data, and blood chemistry data, to a patient records server located remotely from the patient. Many known systems also lack a mechanism by which a physician can remotely and securely access such data. Thus, a need has arisen for a system and method for performing virtual medical examinations which addresses the foregoing issues.

SUMMARY

Embodiments of a method for permitting a real-time virtual medical examination using a patient device and at least one diagnostic device are disclosed herein. In one such embodiment, the method includes receiving, at the patient device, a signal transmitted from the at least one diagnostic device and generating diagnostic information based on the received signal. The method also includes encrypting the diagnostic information, establishing communication over a network between the patient device and a first remote server, establishing a video conferencing session via a second remote server and transmitting the encrypted diagnostic information to the first remote server.

Embodiments of an apparatus for receiving a real-time virtual medical examination using at least one diagnostic device are also disclosed herein. In one such embodiment, the apparatus includes a memory and at least one processor configured to execute instructions stored in the memory to receive a signal transmitted from the at least one diagnostic device and generate diagnostic information based on the received signal. The at least one processor is also configured to encrypt the diagnostic information, establish communication over a network between the patient device and a first remote server, establish a video conferencing session via a second remote server and transmit the encrypted diagnostic information to the first remote server.

Embodiments of a method for permitting a real-time virtual medical examination by a health care provider using health care provider device on a patient using a patient device are also disclosed herein. In one such embodiment, the method includes establishing communication over a network with the health care provider device and the patient device and receiving, from the patient device, encrypted diagnostic information related to the patient. The encrypted diagnostic information is generated from at least one diagnostic device. The method also includes transmitting the encrypted diagnostic information to the health care provider device.

Embodiments of a system for performing a real-time virtual medical examination are also disclosed herein. In one such embodiment, the system includes a network permitting communication between a patient device and a physician device. The patient device is configured to generate encrypted diagnostic information based on a signal transmitted from at least one diagnostic device received signal. The system also includes a first server in communication with the network and configured to receive the encrypted diagnostic information from the patient device and transmit the encrypted diagnostic information to the physician device. Further, the system includes a second server configured to permit a video conferencing session between the patient device and the physician device.

Embodiments of a method for advertising medical information on a patient device are also disclosed herein. In one such embodiment, the method includes generating at least one advertisement related to a health-related product or service and enabling a user to purchase the health-related product or service via a patient device, the patient device operable to permit a real-time virtual medical examination.

These and other embodiments will be discussed in additional detail hereafter.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION

Described herein are systems, methods and apparatuses for performing virtual medical examinations. The systems, methods and apparatuses generally involve the secure transmission of patient diagnostic information by a patient remotely located from a treating physician and the secure retrieval and viewing of the data by the physician. The systems, methods and apparatuses also generally involve secure videoconferencing to allow the physician to remotely conduct a medical examination in real-time, thereby allowing the physician to provide health instruction information by, for example directing the examination, providing therapeutic instructions and any other instructions to the patient.

Figure 1:
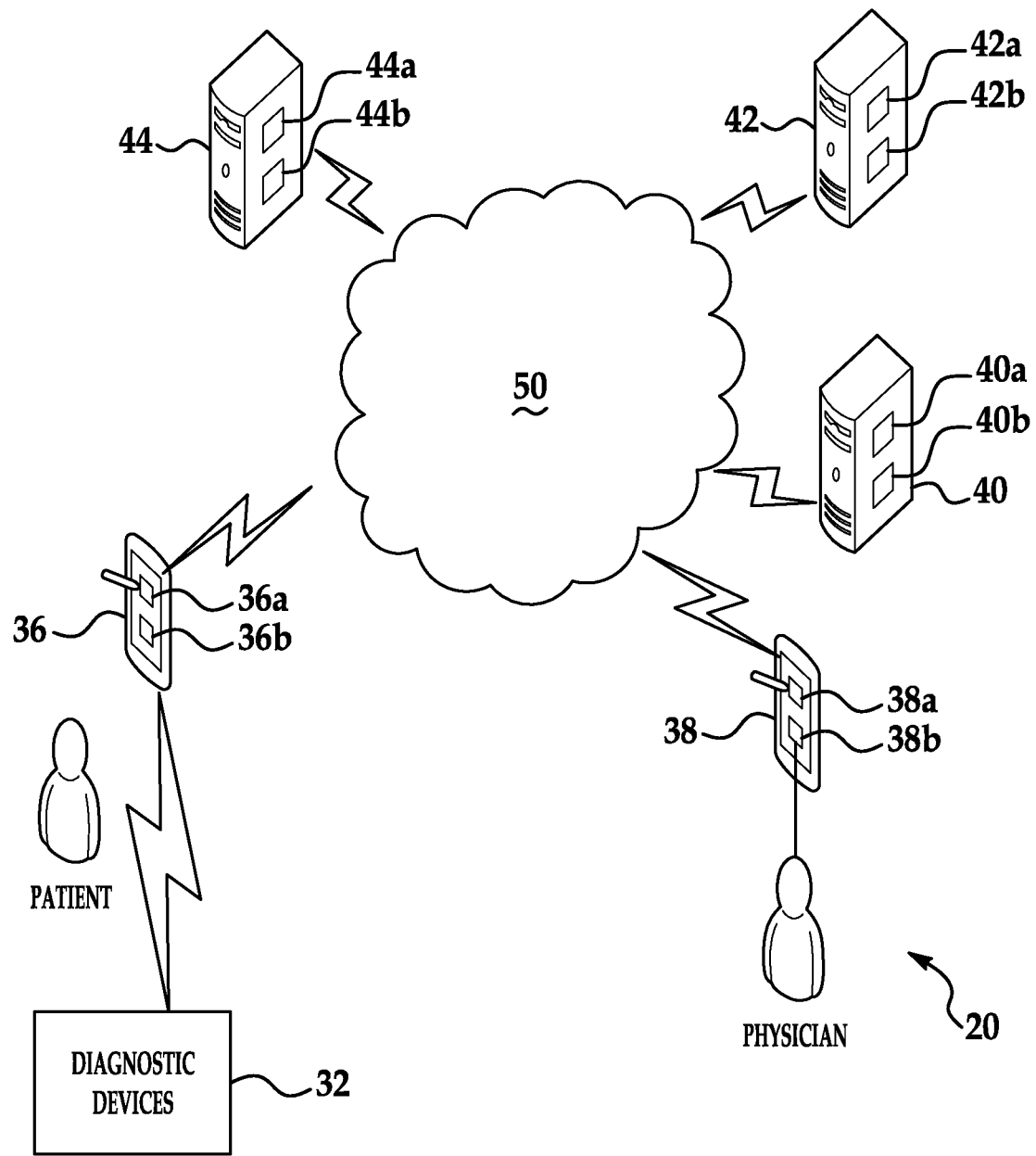
FIG. 1 is a diagram of a system for performing virtual medical examinations in accordance with one embodiment.

Referring to FIG. 1, a virtual medical examination system 20 is depicted. The system can include one or more diagnostic devices 32 that are configured to generate patient diagnostic information, a remote patient device 36, a physician device or healthcare provider device 38, a patient records server 40, a videoconferencing server 42 and a remote content manager server 44. Diagnostic devices 32, remote patient device 36, physician device 38, patient records server 40, videoconferencing server 42 and remote content manager server 44 can all be connected either directly or indirectly via a network 50.

Remote patient device 36, physician device 38, patient records server 40, videoconferencing server 42 and remote content manager server 44 may each be a computer having an internal configuration of hardware including a processor such as a central processing unit (CPU) and a memory. Accordingly, remote patient device 36 can have a CPU 36a and a memory 36b, physician device 38 can have a CPU 38a and a memory 38b, patient records server 40 can have a CPU 40a and a memory 40b, videoconferencing server 42 can have a CPU 42a and a memory 42b and remote content manager server 44 can have a CPU 44a and a memory 44b. CPUs 36a, 38a, 40a, 42a and 44a can be a controller for controlling the operations of patient device 36, physician device 38, patient records server 40, videoconferencing server 42 and remote content manager server 44, respectively. CPUs 36a, 38a, 40a, 42a and 44a can each be connected to memories 36b, 38b, 40b, 42b and 44b, respectively, by, for example, a memory bus. Memories 36b, 38b, 40b, 42b and 44b can store data and program instructions which are used by CPUs 36a, 38a, 40a, 42a and 44a, respectively. Other suitable implementations of patient device 36, physician device 38, patient records server 40, videoconferencing server 42 and remote content manager server 44 are possible. For example, in one embodiment, patient records server 40, videoconferencing server 42 and remote content manager server 44 can be integrated into one server.

Exemplary diagnostic devices 32 include electrocardiographs (ECG), pulse oximeters, spirometers, sphygmomanometers, weight scales, stethoscopes, blood chemistry analyzers, microscopes, ultrasounds probes, etc. The diagnostic devices 32 can include a patient diagnostic information wireless transmitter for transmitting patient diagnostic information to a remote patient device 36. Communications between diagnostic devices 32 and patient device 36 can be wired or wireless.

Wireless communications between diagnostic devices 32 and patient device 36 may be provided using various protocols and other wireless technologies, including 3G and 4G wireless technologies and the IEEE series of wireless technologies. More particularly, wireless communications may take place over a CDMA, EDGE, EV-DO, GPRS, GSM, UMTS, W-CDMA, or a 1xRTT network as well as an IEEE 802.11 (WiFi), 802.15 (a BLUETOOTH™ protocol and ZIGBEE™ protocol), 802.16 (WIMAX™ standard) or 802.20 (MBWA) network. In the example shown in FIG. 1, wireless communications diagnostic devices 32 and patient devices 36 will take place using BLUETOOTH™ technology, but the embodiments disclosed herein are not to be limited to the BLUETOOTH™ protocol.

BLUETOOTH™ communications have certain features that can be beneficial in many implementations of system 20, including a lack of wires, security features such as secure simple device pairing and adaptive frequency hopping, and an effective device to device transmission range of up to about 300 feet. Using the BLUETOOTH™ protocol, suitable diagnostic devices 32 can be identified and paired with the remote patient work stations 36. Suitable BLUETOOTH™-enabled diagnostic devices 32 can be supplied by QRS Diagnostics of Plymouth, Minn.

In other embodiments, rather than communications between diagnostic devices 32 and patient device 36 occurring directly, communications may occur directly via, for example, a local wireless signal gateway (not shown). The wireless signal gateway can be connected to network 50 and is generally in close proximity to diagnostic devices 32 at the time of their transmission of diagnostic information. In one embodiment, the wireless signal gateway is a BLUETOOTH™-enabled wireless signal gateway that may operate external to the patient device 36 hardware as a separate entity or can be integrated into patient devices 36 to allow for long-range transmission of patient diagnostic information to an internet server (not separately shown in FIG. 1), and ultimately, to patient records server 40. One suitable BLUETOOTH™ internet gateway that may be used is the Gigaset-One Bluetooth Gateway supplied by Siemens.

When communication between diagnostic device 32 and patient device 36 is via a wireless protocol, diagnostic device 32 and patient device 32 can be within a suitable distance from one another to permit communication. For example, in one embodiment, diagnostic device 32 and patient device 32 are no more than 90 feet one another although other suitable distances are possible. Because diagnostic devices 32 have a relatively limited transmission radius, the transmission of patient diagnostic information from diagnostic devices 32 to patient devices 36 need not be encrypted. However, patient diagnostic information transmitted from diagnostic devices 32 to patient records server 40 can be encrypted to prevent undesired access by other users of network 50. One encryption method includes https (hypertext transfer protocol secure). However, other encryption methods may be used. In one embodiment, wireless signals can secured via unique user identifiers for patient diagnostic peripheral devices 32.

In one implementation, the diagnostic devices 32 and patient devices 36 utilize the Bluetooth Health Device Profile for transmitting medical data. The Bluetooth Health Device Profile has been standardized by Bluetooth SIG, the industrial association for Bluetooth manufacturers. The Health Device Profile enables a range of additional functions such as exact chronological synchronization of several BLUETOOTH™ connected medical sensors or the option of transferring different medical data in parallel via a Bluetooth interface which is necessary when several diagnostic devices generate patient diagnostic information simultaneously. The Health Device Profile consists of one part that specifies transfer protocols used for medical data in the BLUETOOTH™ stack and another part that describes the structure of the actual medical data.

Patient records server 40 is connected to network 50 and can include a number of patient data files stored in a computerized database. The files may be organized by a variety of methods. However, in one implementation, each patient's files are associated with patient identification data, which can be a unique identifier, such as a numeric or alphanumeric identifier. The patient identifier allows a physician or any other health care provider (e.g. nurse, health care administrator, pharmacist surgeon etc.) to retrieve specific data for a desired patient. Patient diagnostic information transmitted from diagnostic devices 32 can be transmitted in association with a patient identifier so that patient diagnostic information received by patient records server 40 is associated with the specific patient for whom the diagnostic data was generated.

Network 50 may take a variety of forms such as a local area network, wide area network, or the Internet. When network 50 is, for example, the Internet medical examinations can be conducted between physicians and patients who are geographically situated at long distances from one another. In the case where network 50 is the internet, patient records server 40 is referred to as a patient records internet server. In such cases, patient records internet server 40 can be assigned a unique internet protocol address to which wireless signal transmissions from patient device 36 are directed when patient diagnostic information is generated by diagnostic devices 32.

Additionally, other networks can be interfaced with or completely replace network 50. For example, when physician device 38 is a handheld device such as a mobile phone, PDA, smart phone or any other suitable handheld device, network 50 can be a mobile communications network and can include one or more base stations (e.g. macrocell, femtocell, microcell, picocell, etc.). Physician device 38 can send communications to network 50 via the mobile communications network or other transmitting/receiving tower. For example, radio waves can be used to transfer signals between physician device 38 through one or more base stations in the mobile communications network, which can them transmit the communications to network 50. Physician device 38 may also communicate in any other suitable manner, for example, in one embodiment, physician device may communicate via satellite. Further, for example, physician device 38 can connect directly to network 50 (e.g. via 3 g or 4 g services).

When physician device 38 is a handheld device, it can include a subscriber identity module (SIM) card, which can be equipped with encryption/decryption programming. This encryption/decryption programming can be used to authenticate the handheld device and can be in addition to the encryption and decryption of diagnostic information and health instruction information as will be discussed in more detail below. In some embodiments, the SIM card can be used to perform the encryption/decryption of the diagnostic information and health instruction information.

The SIM card can be in a form that is removable by the user, which can make it possible to carry mobile subscription information and data through different types and generations of handheld devices. Alternatively, the SIM card can be integrated into the handheld device. The SIM card can, for example, contain a microchip that houses a processor (e.g. microprocessor) and a memory. The memory can have instructions stored thereon, that when executed by the processor encrypt voice and data transmissions, which can assist in preventing third parties from intercepting transmissions. The SIM, as discussed previously, can identify the user to the mobile communications network as a legitimate user. Each SIM card can be equipped with an additional memory such as EEPROM (Electrically Erasable Programmable Read-Only Memory), which can contain additional information about the device. For example, EEPROM can store an IMSI (International Mobile Subscriber Identification), a PIN (Personal Identification Number), an international access entitlement, a priority class, and subscriber information.

As indicated in FIG. 1, virtual medical examination system 20 includes a physician device 38, which can be a hand-held computing device with a visual display. Device 38 can be programmed to allow the physician to access, retrieve, decrypt, and view patient diagnostic information from patient records server 40. Device 38 can be connected to network 50. In one embodiment, physician device 38 is wirelessly connected to the interne and configured to generate the IP address of patient record server 40 for the retrieval of patient diagnostic information. Physician device 38 can also be programmed to decrypt patient diagnostic information received from patient records server 40 via network 50 so the data can be displayed on physician device 38. Thus, the networking of physician device 38 with patient records server 40 and diagnostic devices 32 allows for the secure transmission of patient diagnostic information to patient record server 40 and the secure retrieval of patient diagnostic information from patient record server 40 by a physician. Patient record server 40 may be programmed to require one or more passwords or other sign-in credentials to verify the identity of the physician and ensure that access to patient diagnostic information is appropriately limited to authorized individuals. The transmission of patient diagnostic information to patient records server 40 and the subsequent retrieval of the data from patient records server 40 by a physician can occur in real-time.

Virtual medical examination system 20 can also be configured to allow a patient and physician to conduct video conference calls. In one implementation, system 20 is configured to allow a patient and physician to conduct secure, encrypted video conference calls that cannot be monitored or accessed by unauthorized third parties. In one example, the encryption provides for HIPAA compliant transmission of patient information. In another implementation, multiple authorized parties may participate in the video conference calls, thereby allowing multiple physicians (who may be remote from one another and from the patient) to collaborate and/or jointly conduct an examination of the patient.

In the illustrative example of FIG. 1, a videoconferencing server 42 is provided which allows a patient and physician to conduct a secure encrypted video conference call over network 50. A "secure" videoconference server includes features that prevent or minimize the likelihood that third parties will be able to intercept information transmitted from one party to another during the videoconference. Such interception is sometimes referred to as a "man in the middle attack" or "packet sniffing." In some embodiments, network 50 is the Internet, in which case the videoconferencing server 42 may be referred to as a videoconferencing internet server. In one embodiment, the patient speaks into a microphone (which may be provided on device 36), and stands in the field of view of a camera (which may also be provided on device 36) to generate voice and video data. The voice and video data is encrypted, for example by using https, and transmitted to video conferencing server 42 via network 50. Https can create a secure channel over an unsecure network, such as the internet. The trust inherent in HTTPS is based on major certificate authorities which come pre-installed in browser software, which allows users to confirm the security of the connection if (1) the user trusts that their browser software correctly implements HTTPS with correctly pre-installed certificate authorities; (2) the user trusts the certificate authority to vouch only for legitimate websites without misleading names; (3) the website provides a valid certificate (an invalid certificate shows a warning in most browsers), which means it was signed by a trusted authority; (4) the certificate correctly identifies the website; and (5) either the intervening hops on the Internet are trustworthy, or the user trusts that the protocol's encryption layer (TLS or SSL) is unbreakable by an eavesdropper.

A physician can use device 38 to receive voice and video data from the patient. The voice and video data is transmitted in encrypted form, from videoconferencing server 42 to device 38. Device 38 includes a display screen for viewing video images of the patient and a speaker for listening to voice communications from the patient. The physician speaks into a microphone (which may be provided on device 38) and stands in the field of view of a camera (which may also be provided on device 38) to generate voice and video data. The voice and video data are encrypted by device 38 and transmitted to video conferencing server 42 via network 50. The encrypted voice and video data is then received and decrypted by patient device 36 via network 50. Patient device 36 can include a visual display for viewing images of the physician and a speaker for listening to voice communications from the physician.

Videoconferencing server 42 can be a computer server that is connected to network 50. Video conferencing server 42 can be a video conferencing internet server, as in the case where network 50 is the internet. Suitable servers are supplied by Visual Systems Group, Inc., Radvision Ltd., and Tandberg. In one embodiment, a video conference call between a patient and physician is conducted using a single, secured TCPIIP connection. In another embodiment, videoconferencing server 42 is configured to allow multiple parties to participate in a secure virtual medical examination. This option is particularly useful for situations in which a primary physician and a secondary physician (e.g., a consultant or specialist) are geographically remote from one another and from the patient. In one example, a virtual conference room is provided which allows for a multi-participant secure meeting. In this manner, virtual medical examination system 20 allows for multi-physician medical examinations and real-time consultations which previously may have been cost prohibitive or otherwise infeasible.

In certain implementations, video conferencing server 42 is configured as a plurality of geographically distributed video conferencing servers that are interconnected via the internet. The use of distributed video conferencing servers allows for load balancing of the various servers to maintain optimum performance. Video conferencing server 42 can be configured to require users to provide passwords or other evidence of their authorization to participate in a video conference to better ensure that the confidentiality of patient information is not compromised. In one embodiment, videoconferencing server 42 is a session-initiation protocol ("SIP") server. Other protocols for establishing video conferencing are also available. For example, video conferencing can be established using IP Multimedia Subsystem (IMS), Media Gateway Control Protocol, Real-Time Transport Protocol (RTP) or any other suitable protocol.

In one embodiment, patient device 36 and physician device 38 receive their content from a remote content manager server 44 connected to network 50. In one embodiment, when devices 36 and 38 are activated, they retrieve programs that launch graphical user interfaces from content manager server 44 via network 50. This allows for the centralized updating of the software and interfaces used by the devices 36 and 38 and avoids the necessity of individually revising the software used in devices 36 and 38. In one embodiment, network 50 is the Internet, in which case content manager server 44 may be referred to as a content manager internet server. In other embodiments, content manager server 44 supplies devices 36 and 38 with one or more programs that provide a common platform to facilitate that receipt, transmission, and display of patient data and patient/physician voice and video data. Patient device 36 and physician device 38 may take a variety of forms, such as a standard personal computer, tablet computer, smartphone, etc. In one embodiment, patient device 36 and physician device 38 include a visual display, a camera, and a speaker and patient navigation via screen-displayed icons.

In one embodiment, devices 36 and 38 are handheld computing devices such mobile phones, PDAs, smartphones, tablets, notebooks, computers, netbooks or any other suitable communication device. One suitable type of patient device 36 or physician device 38 is, for example, 10.4" Intel® Atom™ N450 Portable Medical PC. Other suitable devices of varying size and architecture are available. For example, a 17" Portable Medical PC can be used in lieu of the 10.4" Portable Medical PC. Another type of suitable device includes a TFT (thin film transistor) LCD resistive touch screen display and an integrated BLUETOOTH™-enabled wireless transmitter. Another suitable patient device 36 or physician device 38 includes an integrated BLUETOOTH™ module, a 2.0 Megapixel CMOS camera, and a 12 Active Matrix Panel resistive touch screen visual display. It also includes a bar code scanner that facilitates the reading of patient identification information from bar codes.

Figure 2:
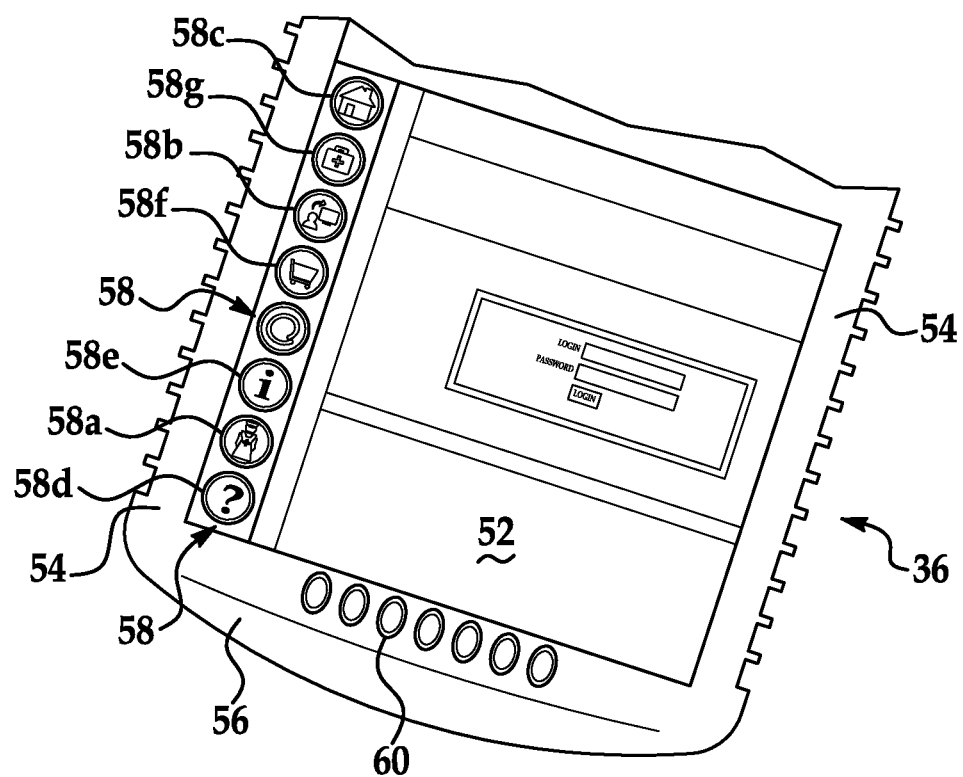
FIG. 2 is a schematic diagram of a patient device or a physician device used in the system of FIG. 1.

Referring to FIG. 2, an exemplary patient device 36 is shown, which also may also be used as a physician device 38. Patient device 36 includes a visual display 52 which can include a touch screen. Plastic side grips 54 are provided to facilitate hand gripping of device 36. Visual display 52 may include a screen with one or more icons 58 that allow the user to initiate various operations. For example, icons 58 can include a collect patient diagnostic information icon 58a, an initiation of a video conference call 58b, a return to home icon 58c, a help icon 58d, an internet icon 58e (i.e. to access the Internet), a shopping cart icon 58*f* (i.e. to purchase items and/or services) and a health record information icon 58*g* to view current and historical patient diagnostic information. Other icons are also possible. Speaker 56 is provided to receive voice communications from a physician, and buttons 60 are provided to allow the user to initiate operations (in addition to or instead of graphical icons 58).

Figure 3:
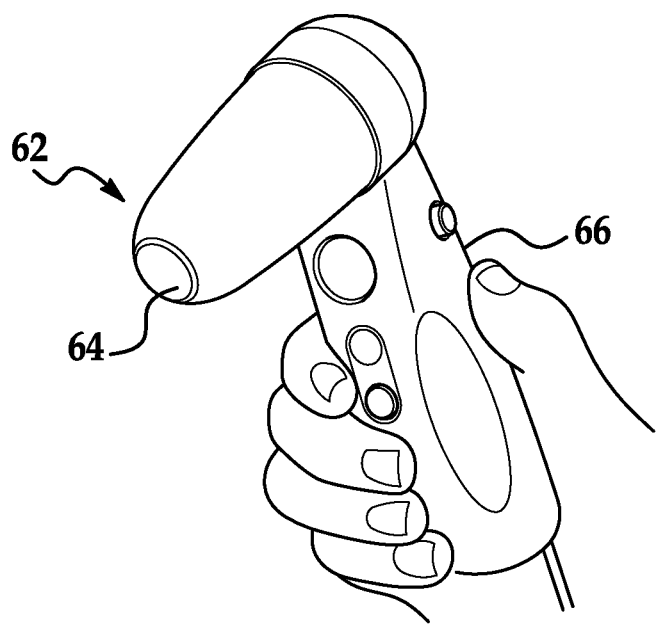
FIG. 3 is a schematic diagram of an exemplary diagnostic device for use in the system of FIG. 1.

During certain examinations, it may be desirable to transmit images of a patient's body to the treating physician. In certain cases, a camera mounted on or integrally provided with device 36 may be sufficient to generate the necessary images. In other cases, however, it may be desirable to obtain and transmit magnified images to the physician. Thus, in certain embodiments, diagnostic devices 32 include a digital microscope 62, as shown in FIG. 3. Digital microscope 62 can include a lens section 64 and a handle 66. Digital microscope 62 can also include a wireless transmitter, which is Bluetooth-enabled. Thus, in certain embodiments, digital microscope images generated by digital microscope 62 can be received and encrypted by device 36 and transmitted to videoconferencing server 42. The images can be then received from videoconferencing server 42 and decrypted by physician device 36 for display thereon. A separate recording server may also be provided to record the digital microscope images (or any other transmission from the video conference call) for subsequent storage in patient records server 40. Alternatively, the digital microscope images can be stored directly in patient records server 40. In accordance with one example, the specific patient-physician video and voice communications from a video conference may be stored with the patient's medical records in patient records server 40 for subsequent retrieval and review, thereby providing an accurate history of patient-physician communications.

As mentioned previously, patient device 36 and physician device 38 can include a graphical user interface (GUI) supplied by, for example, content manager server 44 which facilitates the initiation of desired functions. Referring to FIGS. 4A-D, exemplary GUI screen from patient device 36 and/or physician device 38 are shown.

Figure 4A:
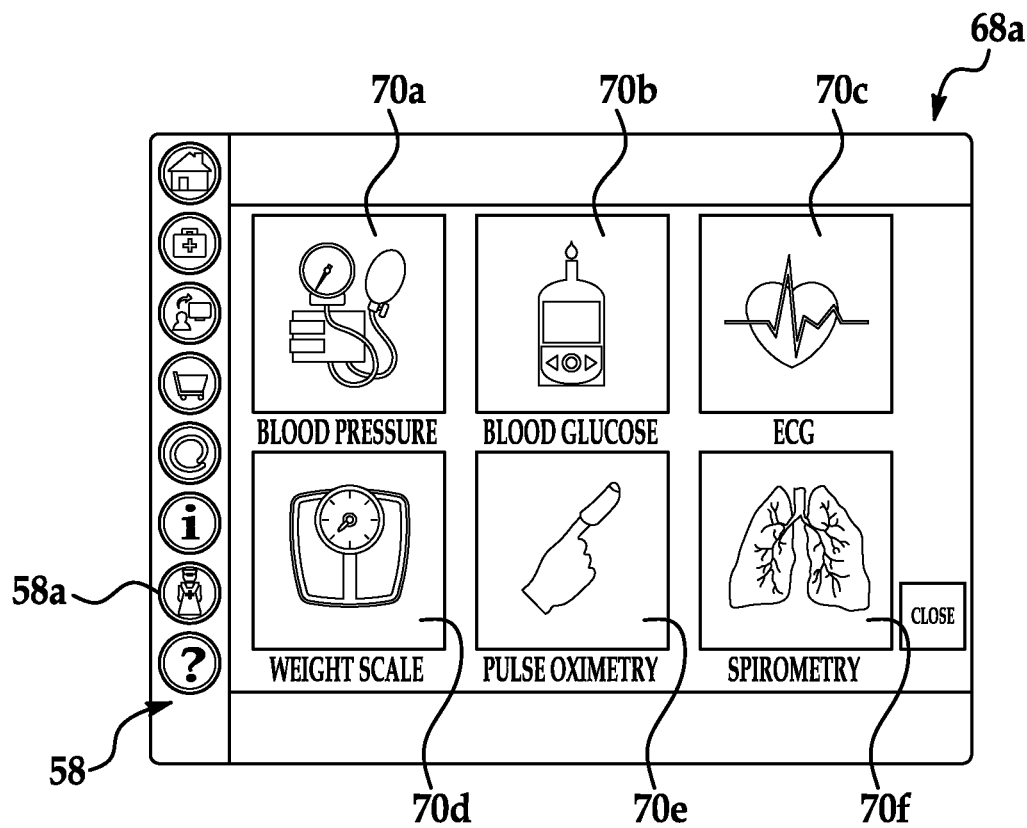
FIGS. 4A-4D are exemplary graphical user interface screens on the patient device of FIG. 2.

FIG. 4A is a screen 68*a* on patient device 36 presented to a patient who has selected the collect patient diagnostic information icon 58*a*. When collect patient diagnostic information icon 58*a* is selected, the patient is presented with one or more selectable touch screen buttons so that patient device 36 can identify that a diagnostic procedure will be performed by the patient using diagnostic device 32. In this example, the patient is presented with the option to take their blood pressure by selecting button 70*a*, take their blood glucose by selecting button 70*b*, their ECG by selecting button 70*c*, their weight by selecting button 70*d*, their pulse/oxy by selecting button 70*e* or their spirometer reading by selecting button 70*f*. Each button can receive patient diagnostic information specific to the diagnostic procedure being performed. In some instances, alterative or more or less diagnostic procedures can be displayed to the patient on screen 68*a*.

Figure 4B:
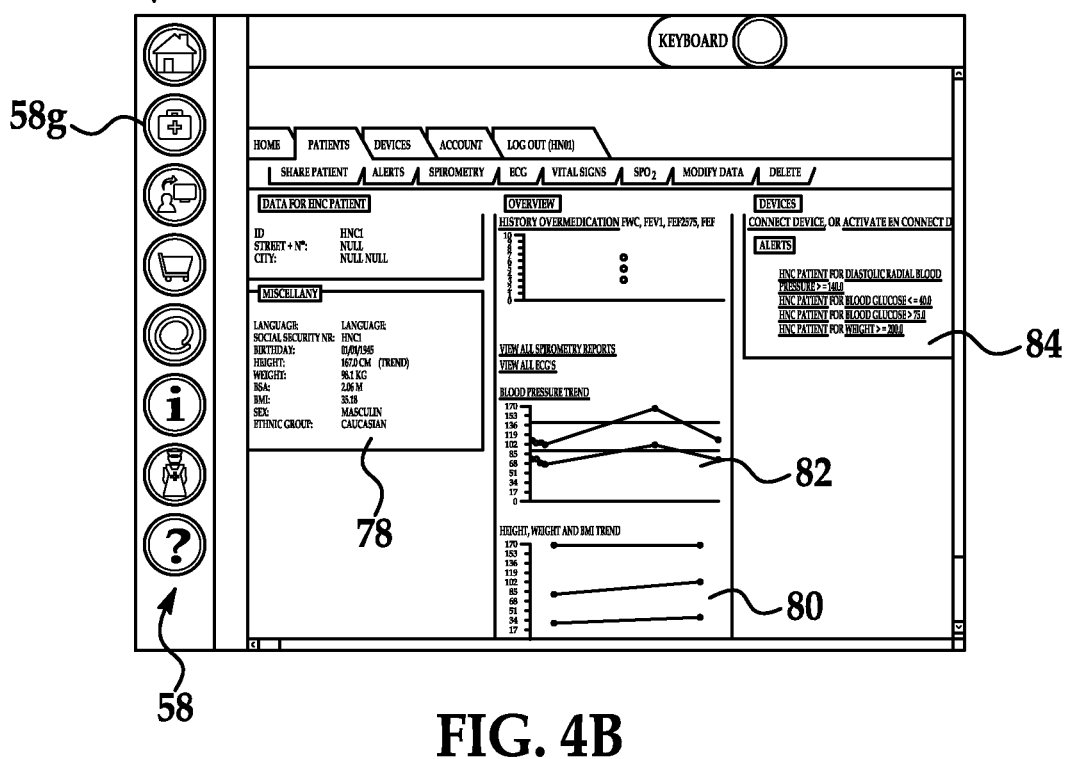

FIG. 4B is a screen 68*b* on patient device 36 presented to a patient who has selected the health record information icon 58*g*. When the health record information icon 58*g* is selected the patient is able to view current or historical data related to the diagnostic procedures that have been performed using diagnostic devices 32. For example, screen 68*b* includes patient data 78 such as name, birthday, height, weight, etc., height, weight. Screen 68*b* also includes trend data for the patient showing developments for, for example, height, weight and bmi trend data 80 or blood pressure trend data 82. Patient can also view alerts 84 related to his/her health. For example, if the patient has abnormally high blood pressure, the alert can indicate that the patient should immediately contact a hospital. Other configurations of screen 68*b* are also possible.

Figure 4C:
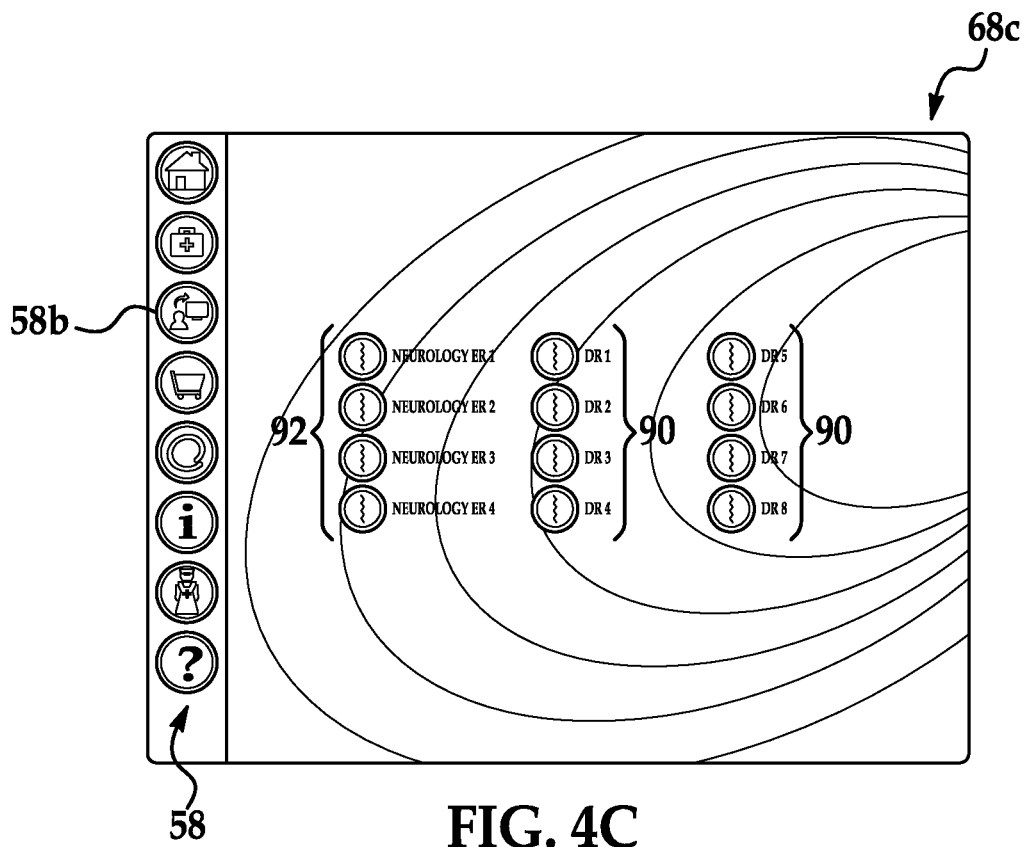

FIG. 4C is a screen 68*c* on patient device 36 presented to a patient who has selected the initiation of a video conference call 58*b*. In this is a graphical user interface screen that allows the user to place a video conference call with a specific doctor conference rooms by selecting one of touch screen buttons 90 or to enter one or more general conference rooms by selecting one of touch screen buttons 92. A similar screen can also be presented on physician device 36. Accordingly, the patient and/or doctor(s) can conduct a video conference if both have entered the same conference room. Communications via the patient and doctor (or between doctors), as discussed previously, are encrypted and secure.

Alternatively to having conference rooms, or in addition, screen 68 can include a key pad section, an icon section, and a speed dial section. The key pad section includes phone button images that can allow the patient to key in the telephone number of the doctor participating in the video conference call. The speed dial section can allow the user to pre-program the phone numbers of selected doctors and to associate a designated "button" with each doctor to provide one-touch dialing. The icon section can include various icons that allow a user to initiate desired operations such as calling 911, accessing a phone directory, initiating video for a video call, taking diagnostic data with a diagnostic device 32, accessing a medical supplies web site to purchase supplies, and accessing health care information.

Figure 4D:
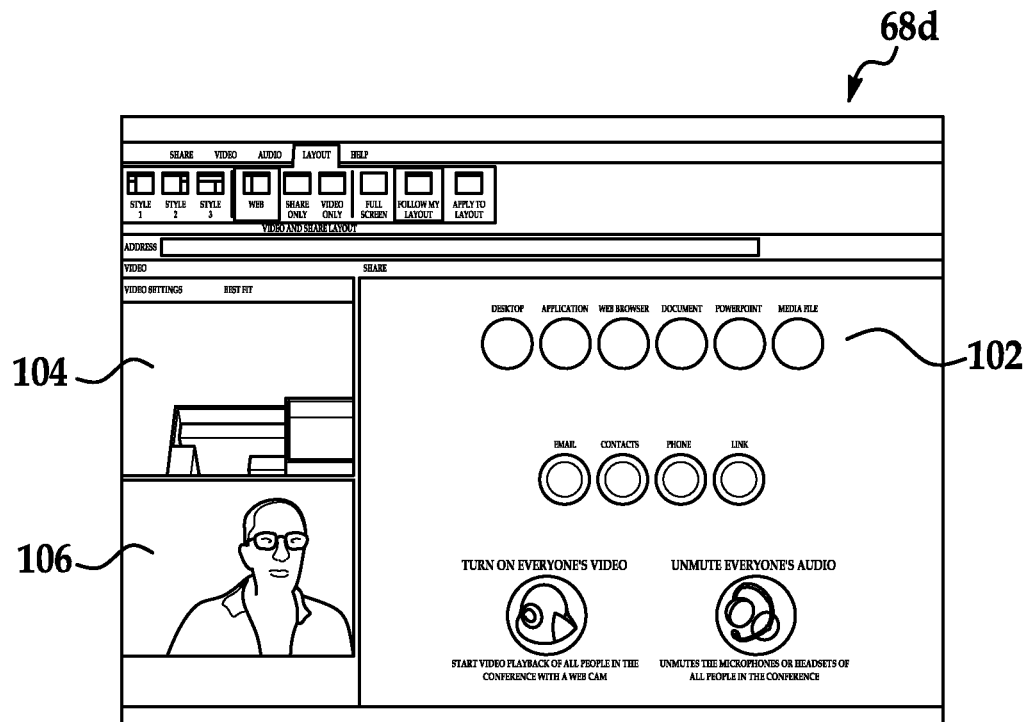

Once a video conference room has been selected, the patient (or doctor) can be presented with a screen 68*d* illustrated in FIG. 4D showing a patient and/or physician device conducting a video conference. In accordance with the example, screen 68*d* includes an icon section 102, and a plurality of video display sections, such as first video display section 104 and a second video display section 106. Video display sections 104 and 106 can display video images of different video conference participants. For example, for patient device 36, video display section 104 may display the primary treating physician, and video display section 106 may display a consulting physician or specialist. In addition, video display section 104 may be used to provide the patient with a video image of himself as generated by a camera on device 36. For a physician device 38, video display section 104 may be used to display the image of the patient generated by a camera located on patient device 36 while video display section 106 may be used to display the image of the patient generated by digital microscope 62. In one embodiment, a GUI screen is provided which allows the physician and/or patient to view video images and patient diagnostic information simultaneously.

Device 36 can also have screens displaying tutorials or advertisements related to diagnostic devices 32. For example, in one embodiment, the GUI on device 36 can display tutorial information for aid in using the diagnostic device so that the patient is able to properly transmit the information to system 20. They tutorial may be interactive or non-interactive. In an interactive tutorial, the tutorial may prompt the user to indicate when they have performed a certain action. The following are exemplary prompts for blood pressure tutorial using a sphygmomanometer device and the prompts that the patient will encounter.

1. Put on cuff, left arm, with pressurizing hose at crook of elbow.

2. Press Power button on 2-in-1; cuff will inflate and slowly deflate.

3. When blood pressure reading shows on screen, press "Blood Pressure" icon.

4. Data will transfer and blood pressure device powers off, and "Successful" message appears on your patient device.

The patient can verify once they have performed a one of the actions. Other tutorials are possible.

Device 36 can also be used to generate advertisements to the patient. For example, if it is determined that the patient's blood glucose level is too high, an advertisement for a blood glucose medication can be generated for display on the device's GUI. The advertisements may be run when device 36 is powered on, periodically when device 36 is running, prior to device 36 shutting down or at any other suitable time. The devices may or may not be tailored specific to the patient. The advertisements may change over time by, for example, an update from the content manager server 42. Alternatively, the advertisements can be pre-programmed into device 36 when, for example, the patient receives device 36.

Figure 5:
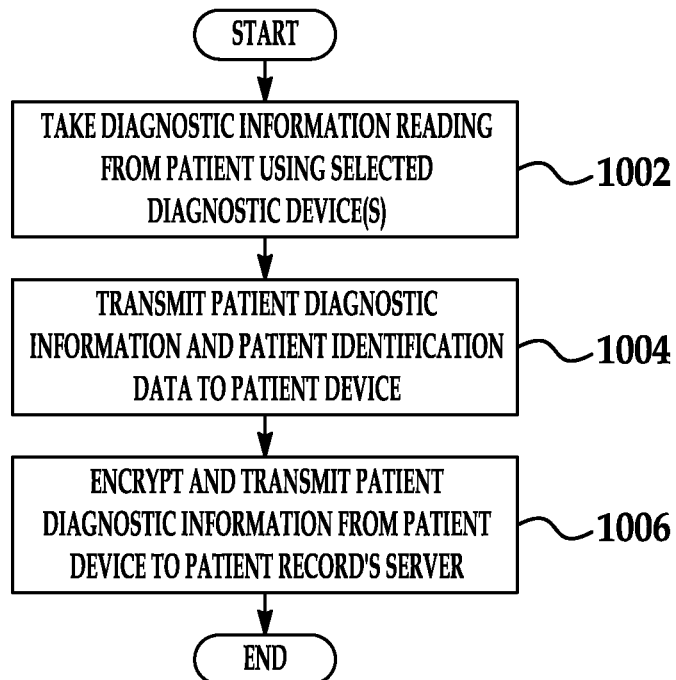
FIG. 5 is a flowchart diagram depicting an exemplary method of generating patient diagnostic information and securely transmitting and storing the data in a patient records server.

Referring to FIG. 5, a method of using virtual medical examination system 20 to generate and securely transmit patient diagnostic information to patient records server 40 will now be described. In accordance with the method, a patient selects one or more diagnostic devices 32 of the type described previously. In step 1002, the patient uses the diagnostic device 32 to generate diagnostic data (e.g., blood pressure, blood chemistry, pulse oximetry, weight, spirometry, etc.). Diagnostic device 32 transmits (wirelessly or via a wired connection) patient diagnostic information to patient device 36.

In step 1004, patient device 36 encrypts patient diagnostic information and information identifying the patient (hereinafter patient identification data) using an encryption protocol such as https. Patient device 36 then transmits the encrypted data to patient record server 40 via network 50, which can be the internet or any other communication network. Patient record server 40 can have a unique network address (e.g., IP address), that allows the patient device 36 to uniquely identify it as the intended recipient of the encrypted patient diagnostic information and patient identification data. The patient record server 40 stores the patient diagnostic information in association with the patient identification data so that the data is accurately identified with the correct patient when retrieved by a health care provider. When the connection between patient device 36 and diagnostic device 32 is wireless, patient can beneficially perform diagnostic tests without having to make a wired connection to the diagnostic device 32 and a computer or other transmitting device. Instead, the patient need only activate the diagnostic device 32 and locate it within the zone of transmission of the patient device 32.

In certain examples, diagnostic devices 32 are pre-configured to generate wireless signals comprising patient identification data that corresponds to a specific patient to which diagnostic devices 32 have been uniquely assigned. For example, each patient may be assigned a unique numeric or alphanumeric code, which corresponds to a particular wireless signal generated by diagnostic devices 32. In one example, the patient files resident in patient record server 40 are setup via the web. When subsequent diagnostics are taken they are applied to the file by opening the utility ready for the diagnostic information to be captured.

Figure 6:
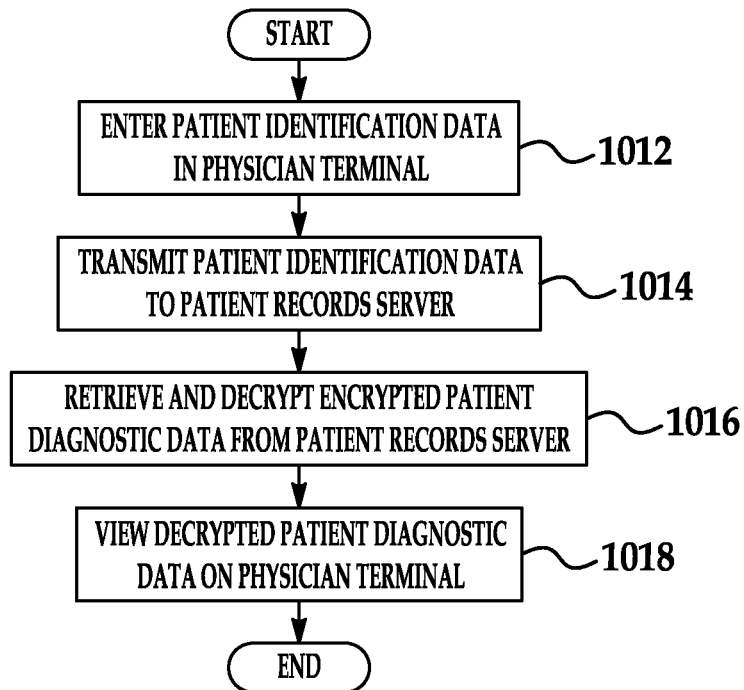
FIG. 6 is a flowchart diagram depicting an exemplary method of securely retrieving patient diagnostic information from a patient records server and displaying the retrieved data on a physician device.

Referring to FIG. 6, a method of securely retrieving patient diagnostic information from patient record server 40 is described. In accordance with the method, a physician can enter patient identification information into physician device 38 such as by using touch screen 52) at step 1012. Next, at step 1012, physician device 38 can transmit (via a wired or wireless connection) the patient identification information to patient record server 40 via network 50. Patient record server 40 can cause a graphical user interface to be displayed on physician device 38 which requests certain physician credential information (e.g., a log-in name and a password). Patient record server 40 may be physically resident at a facility such a hospital or clinic with which the physician is associated, although the physician may be remotely located from server 40 when accessing it. Alternatively, the physician may sign into patient record server 40 before transmitting patient identification data to it.

Once the physician's authorization to review data for a specific patient is confirmed, the data is transmitted in encrypted form to physician device 38. At step 1016, physician device 38 can include executable code (which may be provided by content manager server 44) to allow for the decrypting of encrypted patient diagnostic information. The patient diagnostic information can then be displayed on physician device 38 to be viewed by the physician at step 1018.

Figure 7:
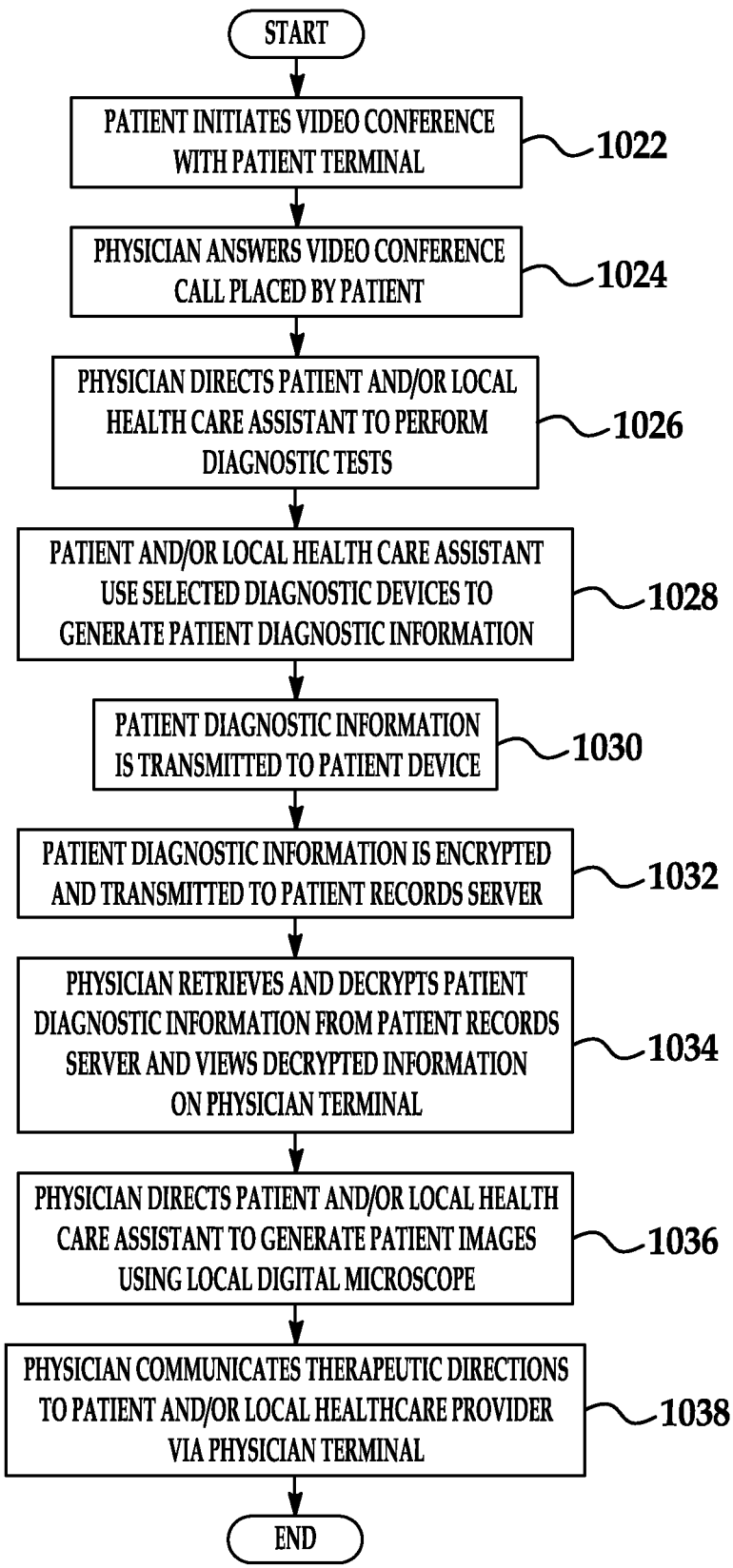
FIG. 7 is a flowchart depicting an exemplary method of performing a virtual medical examination.

Referring to FIG. 7, an exemplary method of performing a virtual medical examination of a remotely located patient is described. In step 1022, the patient initiates a video conference call using patient device 36 as described previously. A conference call is then initiated with videoconferencing server 42. Videoconferencing server 42 transmits data to physician device 38 indicating that a call has been initiated. The patient may then use an icon in icon section 58 to activate a camera on patient device 36 and begin the transmission of encrypted patient video data to videoconferencing server 42.

In step 1024, the physician answers the patient's call by pressing appropriate virtual or physical keys on physician device 38. In certain examples, the patient receives video images from a camera on the physician device 38 in video display section 76 and sees the video data generated by a camera on patient device 36 in video display section 77. Correspondingly, the physician may see video images generated by the camera on patient device 36 in video display section 76 of physician device 38 and video images of herself in video display section 77.

In certain examples, the patient may be at his or her home during the virtual medical examination. In other examples, the patient may be alone during the examination. In additional examples, the patient may be with another individual who can assist in the performance of the examination. In one scenario, the patient is in a clinic or hospital and is assisted by a local health care assistant (e.g., nurse or doctor) in providing the remote physician with the diagnostic data necessary to develop a treatment plan. After taking a verbal medical history from the patient and inquiring about any medical issues that may have prompted the request for an examination, the physician can, for example, provide health instruction information to the patient or local health care assistant. For example, the physician can direct the patient and/or a local health care assistant to perform diagnostic tests on the patient using selected diagnostic devices 32 (step 1026). For example, the physician may direct a local health care assistant to take blood pressure readings or measure the patient's weight. The patient and/or local health care assistant can then use one or more diagnostic devices to generate the patient diagnostic information at step 1028.

As used herein, health instruction information includes any information received from the physician or other health care provider. Health instruction information can be generated from physician device 38 and transmitted to patient device 36 in real-time so that the patient or other health care provider can, administer medication, perform a diagnostic procedure, taking vital signs, manipulate a digital microscope (e.g. digital microscope 62 to a certain region of the patient's body or any other action. In some instances, health instruction information may not necessitate any immediate action by the patient. For example, the physician may indicate through health instruction information that the patient should take their temperature in one hour. However, the health instruction information is transmitted and received by the patient in real-time.

Health instruction information can be in the form of voice, text or image data or any other suitable type of data. For example, when voice data is the form in which health instruction information is formulated, the voice data can be transmitted to video conferencing server 42. Voice data can be oral instructions to the patient. When text or image data is the form in which health instruction information, the text or image data can be transmitted to the patient records server 40. For example, the physician can send a message to a patient to "take blood pressure" rather than communicating the instruction orally. Other suitable techniques for transmitting health instruction information are possible. For example, image data can be sent to video conferencing server 42 rather than patient records server 40.

As discussed previously, transmitters in the diagnostic devices 32 can wirelessly transmit patient diagnostic information generated by diagnostic devices 32 to patient device 36 in association with patient identification information, for example, a unique alphanumeric code assigned to the patient (step 1030). The wireless transmission of diagnostic data to patient device 36 can be performed using the BLUETOOTH™ protocol. The patient device 36 can encrypt the received patient diagnostic information and patient identification data, using an https protocol or any other secure protocol. Thus encrypted, the patient identification data and patient diagnostic information can be transmitted to the patient record server 40 (step 1032). Using physician device 38, the physician can access patient record server 40 upon login using permissions-assigned passwords for safety and confidentiality and can retrieve and decrypt the patient diagnostic information which is then displayed on physician device 38 (step 1034). In certain examples, the patient diagnostic information is also transmitted to the patient device 36, where it is decrypted and displayed to the patient. The concurrent transmission of patient diagnostic information from patient device 36 to physician device 38 while the patient device 36 and physician device 38 exchange information to conduct a secure video conference session are in real-time.

In certain situations, the physician may wish to obtain microscope images of certain areas of the patient's body. In such situations, the physician may direct the patient and/or a local health care assistant (such as an emergency room doctor, a nurse, or a physician's assistant) to manipulate digital microscope 62 (or other diagnostic device 32) to selected regions of the patient's body to obtain the desired microscope images (step 1036). Digital microscope 62 can transmit video data of the images to patient device 36 which then encrypts and transmits the video data to video conference server 42 for subsequent retrieval by the physician and viewing on the physician device 38. At the outset of the call or during the call, the treating physician may ask another health care provider, such as a specialist, to join the video conference. The specialist can access the videoconference server (such as by inputting an IP address or domain name for the videoconference server into his or her computer terminal). After supplying the appropriate authorization credentials (such as a log in and password), the specialist will be connected to the call.

In step 1038, the physician (alone or in conjunction with a consultant or specialist) communicates therapeutic directions to the patient using physician device 38. Alternatively, the physician may consider the information provided during the video conference and may conduct a subsequent video conference to provide therapeutic directions. In another scenario, the physician may conduct a secure video conference with another physician and both physicians may view patient diagnostic information from the patient records server 40 to collaborate and develop a joint treatment plan. The method of FIG. 7 may be used for the diagnosis and treatment of recurring or non-recurring conditions, and it may also be used to perform periodic monitoring of patients with chronic conditions, such as diabetes. The method of FIG. 7 is not limited to the treatment of any one particular condition, and exemplary conditions include diabetes, asthma, hypertension, chronic obstructive pulmonary disease, and heart failure or any other condition Exemplary Application The following is an exemplary application for transmitting patient diagnostic information to a remotely located physician who is using a handheld device such as a mobile phone (e.g. physician device 38). A diagnostic device (e.g., diagnostic device 32), which is BLUETOOTH™-enabled, can wirelessly transmit patient diagnostic information to a patient device (e.g., patient device 36), which is also BLUETOOTH™-enabled. The patient device can encrypt and transmit the patient diagnostic information to a patient information server such as a patient records server 40. The patient information server records the received patient diagnostic information in a patient file and then re-transmits the data to the patient device and a physician device. Access to the patient diagnostic information can be controlled via a set of administrator permissions and all patient data can be shelled within a secure HIPAA compliant environment to ensure confidentiality of data via, for example, encrypted HTTPS communication.

A secure videoconference can be conducted between one or more physicians and a patient in a virtual conference room so that the patient and the physician can access the diagnostic information in real-time during the videoconferencing session. After reviewing patient diagnostic information, a physician, via his physician device, can initiate a videoconference with the patient and/or one or more additional physicians (or other healthcare providers). Each physician can access have access to the diagnostic information and be part of the videoconferencing session via their handheld device. As such, each physician can receive the diagnostic information real-time regardless of their location and review the diagnostic information to provide health instruction information. For example, a physician joining the video conference such as a specialist may request that that a certain diagnostic procedure be performed on the patient that was not requested by the physician who was initially part of the video conference. A recording server (e.g. patient records server 40) can record all voice and video data from the conference. The virtual conference rooms can be provided by a videoconferencing server (e.g., video conferencing server 42) that can provide, for example, secure https encryption of all voice and video data.

The embodiments of remote patient device 36, physician device 38, patient records server 40, videoconferencing server 42 and/or remote content manager server 44 (and the algorithms, methods, instructions etc. stored thereon and/or executed thereby) can be implemented in hardware, software, or any combination thereof including, for example, IP cores, ASICS, programmable logic arrays, quantum or molecular processors, optical processors, programmable logic controllers, microcode, firmware, microcontrollers, servers, microprocessors, digital signal processors or any other suitable circuit. In the claims, the term "processor" should be understood as encompassing any the foregoing devices, either singly or in combination. The terms "signal" and "data" are used interchangeably. Further, portions of remote patient device 36, physician device 38, patient records server 40, videoconferencing server 42 and/or remote content manager server 44 do not necessarily have to be implemented in the same manner.

Further, in one embodiment, for example, remote patient device 36, physician device 38, patient records server 40, videoconferencing server 42 or remote content manager server 44 can be implemented using a general purpose computer/processor with a computer program that, when executed, carries out any of the respective methods, algorithms and/or instructions described herein. In addition or alternatively, for example, a special purpose computer/processor can be utilized which can contain specialized hardware for carrying out any of the methods, algorithms, or instructions described herein.

Further, all or a portion of embodiments of the present invention can take the form of a computer program product accessible from, for example, a computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or a semiconductor device. Other suitable mediums are also available.

The above-described embodiments have been described in order to allow easy understanding of the present invention and do not limit the present invention. On the contrary, the invention is intended to cover various modifications and equivalent arrangements included within the scope of the appended claims, which scope is to be accorded the broadest interpretation so as to encompass all such modifications and equivalent structure as is permitted under the law.

The invention claimed is:

1. A method for permitting a real-time virtual medical examination using a handheld patient device and at least one diagnostic device, comprising:
receiving, at the handheld patient device, a signal transmitted from the at least one diagnostic device;
generating, by the handheld patient device, diagnostic information based on the received signal;
encrypting, by the handheld patient device, the diagnostic information;
establishing communication over a network between the handheld patient device and a remote server;
establishing communication over the network between the handheld patient device and a video conferencing server comprised in a plurality of geographically distributed video conferencing servers;
establishing a video conferencing session via the video conferencing server in communication with the handheld patient device;
encrypting and transmitting, by the handheld patient device, first voice and video signals generated during the video conferencing session to the video conferencing server, the first voice and video signals being encrypted using a hypertext transfer protocol secure method;
receiving and decrypting, by the handheld patient device, encrypted second voice and video signals generated during the video conferencing session from the video conferencing server, the second voice and video signals being encrypted using a hypertext transfer protocol secure method; and
transmitting, by the handheld patient device, the encrypted diagnostic information to the remote server.

2. The method of claim 1, wherein transmitting the encrypted diagnostic information further comprises: concurrently conducting the video conferencing session while transmitting the encrypted diagnostic information to the remote server.

3. The method of claim 1, wherein encrypting the diagnostic information comprises encryption using a hypertext transfer protocol secure method.

4. The method of claim 1, wherein the at least one diagnostic device is a spirometer, a stethoscope, a sphygmomanometer, a blood pressure monitor, a blood chemistry analyzer, a pulse oximeter, an electrocardiograph, an ultrasound probe or a scale.

5. The method of claim 1, wherein the handheld patient device is at least one of a personal computer, a tablet computer, a personal data assistant or a cellular telephone.

6. The method of claim 1, further comprising encrypting diagnostic information within the handheld patient device using a hypertext transfer protocol secure method.

7. The method of claim 1, wherein the remote server is separate from the video conferencing server.

8. A patient device for receiving a real-time virtual medical examination using at least one diagnostic device, comprising:
a memory;
at least one processor configured to execute instructions stored in the memory to:
receive a signal transmitted from the at least one diagnostic device;
generate diagnostic information based on the received signal;
encrypt the diagnostic information;
establish communication over a network between the patient device and a remote server;
establish communication over the network between the patient device and a video conferencing server comprised in a plurality of geographically distributed video conferencing servers;
establish a video conferencing session via the video conferencing server in communication with the patient device, the video conferencing session being conducted in a Health Insurance Portability and Accountability Act of 1996 (HIPAA) compliant encrypted environment;
encrypt and transmit first voice and video signals generated during the video conferencing session to the video conferencing server and receive and decrypt second encrypted voice and video signals generated during the video conferencing session from the video conferencing server, the first and second voice and video signals being encrypted using a hypertext transfer protocol secure method; and
transmit the encrypted diagnostic information to the remote server.

9. The patient device of claim 8, wherein the at least one processor is further configured to execute instructions stored in the memory to: concurrently conduct the video conferencing session while the at least one processor is further configured to execute instructions to transmit the encrypted diagnostic information to the remote server.

10. The patient device of claim 8, wherein the signal from the at least one diagnostic device is transmitted to the patient device via one of a wireless connection and a wired connection.

11. The patient device of claim 8, wherein the at least one processor encrypts the diagnostic information using a hypertext transfer protocol secure method.

12. The patient device of claim 8, wherein the at least one diagnostic device is a spirometer, a stethoscope, a sphygmomanometer, a blood pressure monitor, a blood chemistry analyzer, a pulse oximeter, an electrocardiograph, an ultrasound probe or a scale.

13. The patient device of claim 8, wherein the patient device is a handheld patient device.

14. The patient device of claim 8, wherein the remote server is separate from the video conferencing server.

15. A method for permitting a real-time virtual medical examination by a health care provider using a handheld health care provider device on a patient using a handheld patient device, comprising:
 establishing communication over a network between the handheld health care provider device and a video conferencing server comprised in a plurality of geographically distributed video conferencing servers;
 establishing communication over the network between the handheld patient device and the video conferencing server;
 establishing a video conferencing session via the video conferencing server in communication with the handheld health care provider device and the handheld patient device, the video conferencing session being over the network comprising the video conferencing server, the handheld health care provider device and the handheld patient device, the video conferencing session being conducted in a Health Insurance Portability and Accountability Act of 1996 (HIPAA) compliant encrypted environment;
 encrypting and transmitting, by the handheld patient device, first voice and video signals generated during the video conferencing session over the network, the first voice and video signals being encrypted using a hypertext transfer protocol secure method;
 receiving and decrypting, by the handheld health care provider device, the encrypted first voice and video signals;
 encrypting and transmitting, by the handheld health care provider device, second voice and video signals generated during the video conferencing session over the network, the second voice and video signals being encrypted using a hypertext transfer protocol secure method;
 receiving and decrypting, by the handheld patient device, the encrypted second voice and video signals;
 receiving, by the handheld health care provider device from the handheld patient device, encrypted diagnostic information related to the patient, the encrypted diagnostic information generated from at least one diagnostic device; and
 transmitting, by the handheld patient device, the encrypted diagnostic information to the handheld health care provider device.

\* \* \* \* \*